US009366620B2

(12) United States Patent
Kondo et al.

(10) Patent No.: US 9,366,620 B2
(45) Date of Patent: Jun. 14, 2016

(54) SPECIMEN MEASURING METHOD

(71) Applicant: MURATA MANUFACTURING CO., LTD., Nagaokakyo-Shi (JP)

(72) Inventors: Takashi Kondo, Nagaokakyo (JP); Seiji Kamba, Nagaokakyo (JP); Yuichi Ogawa, Kyoto (JP); Sakura Tomita, Kyoto-Fu (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 14/094,329

(22) Filed: Dec. 2, 2013

(65) Prior Publication Data

US 2014/0084164 A1    Mar. 27, 2014

Related U.S. Application Data

(63) Continuation of application No. PCT/JP2012/059672, filed on Apr. 9, 2012.

(30) Foreign Application Priority Data

Jun. 1, 2011    (JP) ................................ 2011-123143

(51) Int. Cl.
*G01N 21/3577* (2014.01)
*G01N 21/3586* (2014.01)
(Continued)

(52) U.S. Cl.
CPC ............... *G01N 21/3586* (2013.01); *G01J 3/42* (2013.01); *G01N 21/03* (2013.01); *G01N 21/3577* (2013.01); *G01N 2021/035* (2013.01); *G01N 2021/3595* (2013.01)

(58) Field of Classification Search
CPC .......... G01N 21/3586; G01N 21/3577; G01N 21/03; G01N 3/42; G01N 2021/3595; G01N 2021/035
See application file for complete search history.

(56) References Cited

U.S. PATENT DOCUMENTS

| 5,434,411 A | 7/1995 | Miyahara et al. |
| 2002/0001546 A1* | 1/2002 | Hunter et al. ................. 422/102 |

(Continued)

FOREIGN PATENT DOCUMENTS

| CN | 1829909 A | 9/2006 |
| EP | 1 845 364 A2 | 10/2007 |

(Continued)

OTHER PUBLICATIONS

Fumiaki Miyamaru et al., "Effect of Dielectric Thin Films on Reflection Properties of Metal Hole Arrays", Applied Physics Letters, 2010, vol. 96, pp. 021106-1 through 021106-3.

*Primary Examiner* — Yara B Green
(74) *Attorney, Agent, or Firm* — Arent Fox LLP

(57) ABSTRACT

The characteristics of a specimen are measured by holding the specimen on an aperture array structure having apertures, applying an electromagnetic wave to the aperture array structure, and detecting frequency characteristics of the electromagnetic wave reflected by the aperture array structure. A liquid is directly or indirectly attached to at least a part of a first principal surface. The electromagnetic wave is applied from side including a second principal surface. The apertures of the aperture array structure have a size which does not allow the liquid to leak from the first principal surface side to the second principal surface side, and the liquid is attached to the first principal surface of the aperture array structure in a state open to an atmosphere under air pressure.

20 Claims, 8 Drawing Sheets

(51) Int. Cl.
*G01N 21/03* (2006.01)
*G01J 3/42* (2006.01)
*G01N 21/35* (2014.01)

(56) References Cited

U.S. PATENT DOCUMENTS

2007/0229094 A1 10/2007 Kasai et al.
2010/0292936 A1* 11/2010 Jepsen .................... 702/25

FOREIGN PATENT DOCUMENTS

| EP | 2 116 838 A1 | 11/2009 |
| JP | 05-322746 | 7/1993 |
| JP | 2007-010366 A | 1/2007 |
| JP | 2007-163170 A | 6/2007 |
| JP | 2007-304084 A | 11/2007 |
| JP | 2008083020 A | 4/2008 |
| JP | 2009-019925 A | 1/2009 |

* cited by examiner

INCIDENT WAVE        REFLECTED WAVE

INCIDENT WAVE        REFLECTED WAVE

INCIDENT WAVE    REFLECTED WAVE

INCIDENT WAVE    REFLECTED WAVE

INCIDENT WAVE              REFLECTED WAVE

INCIDENT WAVE              REFLECTED WAVE

INCIDENT WAVE　　　　　　　　　REFLECTED WAVE

INCIDENT WAVE            REFLECTED WAVE

INCIDENT WAVE            REFLECTED WAVE

SPECIMEN MEASURING METHOD

This is a continuation of application Ser. No. PCT/JP2012/059672, filed Apr. 9, 2012, the entire contents of which are incorporated herein by reference.

TECHNICAL FIELD

The present invention relates to a specimen measuring method. More particularly, the present invention relates to a method for measuring characteristics of a specimen to be measured by holding the specimen on an aperture array structure having apertures, applying an electromagnetic wave to the aperture array structure, and detecting frequency characteristics of the electromagnetic wave reflected by the aperture array structure.

BACKGROUND ART

Hitherto, characteristics of substances have been analyzed by a method of holding a specimen to be measured on an aperture array structure, applying an electromagnetic wave to the aperture array structure on which the specimen is held, and analyzing a transmittance spectrum of the electromagnetic wave, thereby measuring the characteristics of the specimen. More specifically, there is, for example, a method of applying a terahertz wave to, e.g., a metal mesh filter to which a specimen, such as a protein, is attached, and analyzing a transmittance spectrum of the terahertz wave.

Patent Document 1 (Japanese Unexamined Patent Application Publication No. 2007-010366) discloses a method of holding a specimen to be measured on an aperture array structure (e.g., a metal mesh) having apertures and on a base in close contact with the aperture array structure, applying an electromagnetic wave to the aperture array structure on which the specimen is held, and detecting the electromagnetic wave having transmitted through the aperture array structure, thereby measuring characteristics of the specimen based on a change of frequency characteristics, the change being caused due to the presence of the specimen.

The measuring method disclosed as the related art in, e.g., Patent Document 1 employs, as an index, a change of frequency characteristics caused by the interaction between an electromagnetic field and the specimen near the surface of the aperture array structure. The amount of the change depends on the electromagnetic field that is intensified near the surface of the aperture array structure, the amount of the specimen present in a region of the electromagnetic field, and the value of the complex refractive index. Accordingly, when the amount of the specimen is small, the change of the frequency characteristics is slight and the characteristics of the specimen are difficult to detect.

When the specimen is a liquid, there is known a method using a device called a contact angle meter to measure, e.g., wetness of the liquid. The known method includes the steps of dripping a liquid as a measurement target onto a stationary surface, measuring, with a camera, a size of a round droplet formed by surface tension of the liquid, and calculating a contact angle at an interface between the liquid and the stationary surface. However, it is difficult to measure other characteristics of the liquid as the measurement target at the same time. Another problem resides in that additional equipment, e.g., the camera, is required and the cost is increased.

CITATION LIST

Patent Document

Patent Document 1: Japanese Unexamined Patent Application Publication No. 2007-010366

SUMMARY OF INVENTION

Technical Problem

An object of the present invention is to provide a measuring method which can realize measurement of characteristics of a specimen with high sensitivity and high efficiency even when an amount of the specimen is minute.

Solution to Problem

The present invention provides a measuring method for measuring characteristics of a specimen to be measured by holding the specimen on an aperture array structure having apertures, and by applying an electromagnetic wave to the aperture array structure, and detecting frequency characteristics of the electromagnetic wave reflected by the aperture array structure, wherein the measuring method includes the steps of attaching a liquid directly or indirectly to at least a part of a first principal surface that is one of principal surfaces of the aperture array structure, and applying the electromagnetic wave from side including a second principal surface that is the other principal surface of the aperture array structure, the apertures of the aperture array structure have size not allowing the liquid to leak from the first principal surface side to the side including the second principal surface that is the other principal surface, and the liquid is attached to the first principal surface of the aperture array structure in a state open to an atmosphere under air pressure.

Preferably, the aperture array structure is arranged with the first principal surface being substantially horizontal, the first principal surface is an upper surface of the aperture array structure, and the second principal surface is a lower surface of the aperture array structure.

Preferably, the specimen is attached to at least a part of the first principal surface that is one of the principal surfaces of the aperture array structure, and the liquid is attached to a surface of the specimen. In such a case, preferably, the liquid is water. Furthermore, the characteristics of the specimen are preferably at least one selected from presence or absence, substance amount, surface roughness, and film thickness of the specimen.

The specimen may be the liquid attached to the first principal surface. In such a case, preferably, the liquid is an aqueous solution. Furthermore, the characteristics of the specimen are preferably at least one selected from presence or absence of a solute, surface tension, concentration, and viscosity.

Preferably, the characteristics of the specimen are measured based on changes in the frequency characteristics of reflectance of the electromagnetic wave reflected by the aperture array structure.

Advantageous Effects of Invention

According to the present invention, even when an amount of the specimen is minute (even when a thickness of the specimen from the surface of the aperture array structure is thin), characteristic measurement of the specimen can be realized with high sensitivity and high efficiency.

Moreover, according to the present invention, when the specimen is a liquid, surface tension, concentration, and viscosity of the specimen can be measured in a simpler manner with high sensitivity and high efficiency.

DESCRIPTION OF EMBODIMENTS

Figure 1:
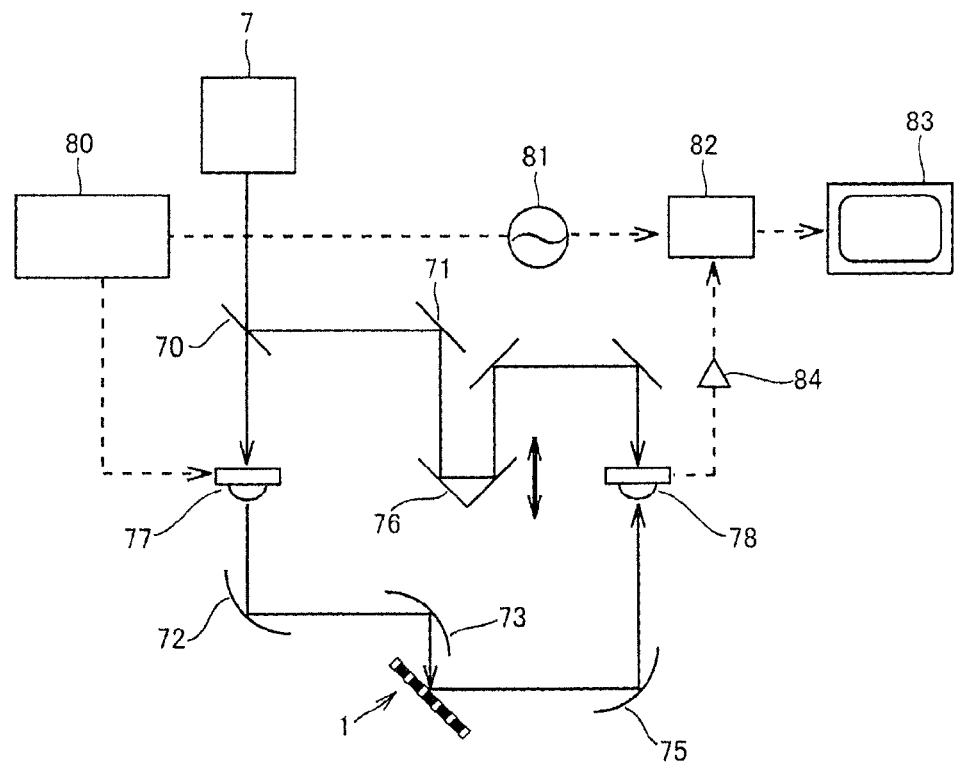
FIG. 1 is a block diagram to explain an outline of a measuring method according to the present invention.

First, an outline of one example of a measuring method according to the present invention will be described below with reference to FIG. 1. FIG. 1 is a block diagram illustrating an overall configuration of a measuring apparatus used to carry out the measuring method according to the present invention. The measuring apparatus utilizes a pulse of an electromagnetic wave (e.g., a terahertz wave), which is generated by irradiating a semiconductor material with a laser beam emitted from a laser 7 (e.g., a short optical pulse laser).

In the configuration of FIG. 1, the laser beam emitted from the laser 7 is branched into two paths by a half mirror 70. One of the branched laser beams is applied to a photoconductive element 77 on the electromagnetic wave generation side, and the other laser beam is applied to a photoconductive element 78 on the reception side via a time delay stage 76 by employing a plurality of mirrors 71 (only one of which is denoted by 71 in FIG. 1 with omission of reference numerals for other mirrors having the similar function). The photoconductive elements 77 and 78 can be each prepared using a general photoconductive element that is obtained by forming, in LT-GaAs (low-temperature-grown GaAs), a dipole antenna with a gap portion. The laser 7 can be prepared, for example, as a laser using a solid, e.g., a fiber type laser or a titanium sapphire laser. The electromagnetic wave may be generated and detected by employing the surface of a semiconductor without an antenna, or an electro-optical crystal such as a ZnTe crystal. A proper bias voltage is applied from a power supply 80 to the gap portion of the photoconductive element 77 on the electromagnetic wave generation side.

The generated electromagnetic wave is converted to a parallel beam by a parabolic mirror 72 and is applied to a periodic structure 1 through a parabolic mirror 73. The terahertz wave having been reflected by the periodic structure 1 is received by the photoconductive element 78 through a parabolic mirror 75. An electromagnetic wave signal received by the photoconductive element 78 is amplified by an amplifier 84 and is then obtained as a time waveform in a lock-in amplifier 82. The obtained time waveform is subjected to signal processing, such as Fourier transform, in a PC (personal computer) 83 including calculation means, whereby, for example, a reflectance spectrum with the flat-plate periodic structure 1 is calculated. To obtain the time waveform in the lock-in amplifier 82, the bias voltage applied from the power supply 80 to the gap portion of the photoconductive element 77 on the electromagnetic wave generation side is modulated (with an amplitude of 5 V to 30 V) by employing a signal from an oscillator 81. With synchronous detection using the modulated voltage, a signal to noise (S/N) ratio can be increased.

The above-described measuring method is a method generally called a terahertz time-domain spectroscopy (THz-TDS). A Fourier transform infrared spectroscopy (FT-IR) may be used instead of the THz-TDS.

The measuring method illustrated FIG. 1 measures reflectance of an electromagnetic wave. Preferably, the reflectance with reflection in the 0-th order direction is measured. In general, given that the lattice interval of a grating is s, an incidence angle is i, the diffraction angle is θ, and the wavelength is λ, a spectrum diffracted by the grating can be expressed by:

$$s(\sin i - \sin \theta) = n\lambda \tag{1}$$

The "0-th order" in the above-mentioned term "0-th order direction" implies the case where n in the above formula (1) is 0. Because s and λ cannot take 0, n=0 holds only when sin i−sin 0=0 is satisfied. Thus, the "0-th order direction" implies the direction given when the incidence angle and the diffraction angle are equal to each other.

The electromagnetic wave used in the measuring method according to the present invention is preferably an electromagnetic wave having a wavelength λ of 1 μm to 300 mm (frequency: 1 GHz to 300 THz), more preferably a wavelength λ of 3 μm to 30 mm (frequency: 10 GHz to 100 THz), and most preferably a wavelength λ of 30 μm to 3 mm or shorter (frequency: 100 GHz to 10 THz).

One practical example of the electromagnetic wave is a terahertz wave that is generated with the optical rectification effect of an electro-optical crystal, e.g., ZnTe, by employing a short optical pulse laser as a light source. Another example of the electromagnetic wave is a terahertz wave that is generated by exciting free electrons in a photoconductive antenna with a short optical pulse laser used as a light source, and by causing a current to be momentarily generated upon application of a voltage to the photoconductive antenna. Still another example of the terahertz wave is one radiated from, e.g., a high-pressure mercury lamp or a high-temperature ceramic.

In addition, the electromagnetic wave applied to the aperture array structure in the measuring method according to the present invention is preferably a linearly polarized electromagnetic wave. The linearly polarized electromagnetic wave may be a linearly polarized electromagnetic wave obtained after an electromagnetic wave emitted from a light source for non-polarized or circularly-polarized light, for example, has passed through a (linear) polarizer, or a linearly polarized electromagnetic wave emitted from a light source for polarized light. For example, a wire grid can be used as the linear polarizer.

In the present invention, the electromagnetic wave is applied to a second principal surface of the aperture array structure, the second principal surface being a principal surface positioned on the opposite side to a first principal surface to which a liquid is attached. In this regard, an angle ($\theta$ denoted in FIG. 5) formed by a propagating direction of the electromagnetic wave and a direction normal to the principal surface of the aperture array structure is 0° to 90° and more preferably 0° to 45°. The reason is that if the angle exceeds 45°, a tendency would arise in generating higher-order diffractions, making a reflectance spectrum complicated, and weakening a reflection signal.

The "characteristics of the specimen" measured in the present invention are, for example, the presence or the absence, substance amount, surface roughness, wetness, surface tension, and film thickness of the specimen. When the specimen is a liquid, the "characteristics of the specimen" are, for example, the presence or the absence of a solute, surface tension, concentration, and viscosity.

When an amount of the specimen is determined in the present invention, it is preferable to prepare a calibration curve in advance based on frequency characteristics that have been obtained by repeating measurements on the specimen in various amounts, and to calculate the amount of the specimen from comparison with the calibration curve.

Aperture Array Structure

The aperture array structure constituting a measurement structure according to the present invention is an aperture array structure having a plurality of apertures that penetrate through the aperture array structure in a direction perpendicular to a principal surface thereof. The entirety of the aperture array structure is usually in the form of a flat plate or a film.

The aperture array structure used in the present invention is a structure in which a plurality of apertures penetrating through the structure in a direction perpendicular to a principal surface thereof are periodically arrayed in the principal surface at least in one direction. However, the apertures are not required to be periodically arrayed over the entirety of the aperture array structure, and they are just required to be periodically arrayed at least in a part of the aperture array structure.

Preferably, the aperture array structure is a quasi-periodic structure or a periodic structure. The term "quasi-periodic structure" implies a structure in which translational symmetry is not held, but an array is orderly kept. Examples of the quasi-periodic structure include a Fibonacci structure as a one-dimensional quasi-periodic structure, and a Penrose structure as a two-dimensional quasi-periodic structure. The term "periodic structure" implies a structure having spatial symmetry such as represented by translational symmetry. The periodic structure is classified into a one-dimensional periodic structure, a two-dimensional periodic structure, and a three-dimensional periodic structure depending on the dimension of the symmetry. The one-dimensional periodic structure is, for example, a wire grid structure or a one-dimensional grating. The two-dimensional periodic structure is, for example, a mesh filter or a two-dimensional grating. Of those periodic structures, the two-dimensional periodic structure is preferably employed. More preferably, a two-dimensional periodic structure including apertures regularly arranged in a vertical direction and a horizontal direction (i.e., in a quadrate array) is employed.

Figure 4:
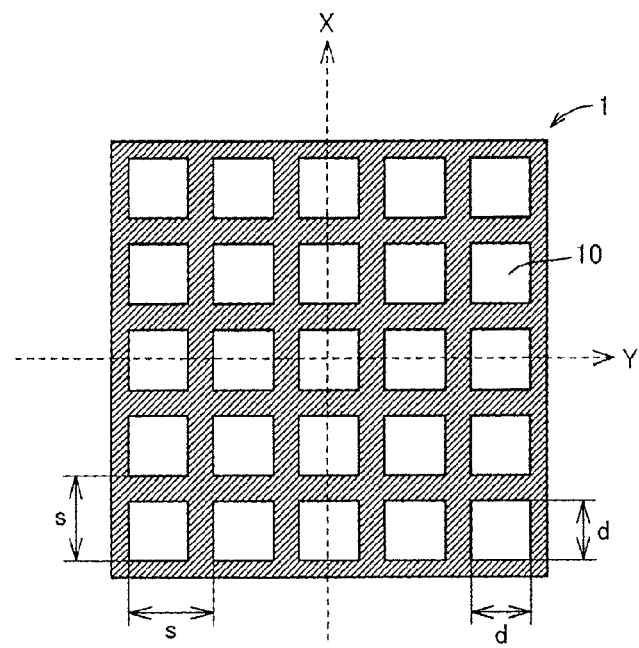
FIG. 4 is a schematic plan view to explain a lattice structure pattern of an aperture array structure.

One example of the two-dimensional periodic structure including the apertures regularly arranged in the quadrate array is a plate-like structure (also called a lattice structure) in which, as illustrated in FIG. 4, apertures 10 are arrayed at constant intervals in a matrix pattern. An aperture array structure 1, illustrated in FIG. 4, is a plate-like structure in which the apertures 10, each having a square shape when viewed from the side including a principal surface of the aperture array structure, are formed at equal intervals in two array directions (i.e., the vertical direction and the horizontal direction in FIG. 4), which are parallel to orthogonal sides of the square shape of the aperture. It is to be noted that the shape of the aperture is not limited to the square shape, and it may be, for example, rectangular, circular, or elliptic. Moreover, the shape of the aperture is not limited to such a symmetrical shape, and the aperture may have a shape provided with a projection or a cutout in its part as described later. In addition, when the apertures are arranged in the quadrate array, the intervals in the two array directions may not be equal to each other, and the apertures may be arranged in a rectangular array.

The thickness (t) of the aperture array structure is preferably not more than a few tenths of the wavelength $\lambda$ of the electromagnetic wave used in the measurement. For example, when the wavelength $\lambda$ of the applied electromagnetic wave is 30 µm, t is preferably not more than 150 µl. If the thickness of the structure exceeds such a range, the intensity of the electromagnetic wave reflected by the structure would be so weakened as to cause a difficulty in detecting the signal in some cases.

The size of each aperture of the aperture array structure is selected such that any of various liquids used in the measurements will not leak from the first principal surface side (e.g., the upper surface side) to the second principal surface side (e.g., the lower surface side). For example, when the aperture array structure is arranged in a state of the first principal surface side providing an upper surface and the second principal surface side providing a lower surface, it is just required that the surface tension of the liquid used in the measurement surpasses the gravity force imposed on the liquid, thus not allowing the liquid to leak to the second principal surface side. Thus, a proper size of the aperture depends on the type of the liquid used in the measurement, the concentration when the liquid is a solution, and so on. In particular, the proportion of an opening area of apertures per unit area on the first principal surface side is preferably 30% to 70% from practical point of view.

Furthermore, the opening size (i.e., a length in the polarization direction of the applied electromagnetic wave) of the aperture on the first principal surface side is preferably not less than 1/10 and not more than 10 times the wavelength $\lambda$ of the electromagnetic wave used in the measurement. If the aperture size is outside the above-mentioned range, the intensity of the electromagnetic wave transmitting through the structure would be so weakened as to cause a difficulty in detecting the signal in some cases.

A lattice interval (pitch) between the apertures is preferably not less than 1/10 and not more than 10 times the wavelength of the electromagnetic wave used in the measurement. If the lattice interval between the apertures is outside the above-mentioned range, the electromagnetic wave would be hard to transmit through the structure in some cases.

The shapes and the sizes of the aperture array structure and each aperture thereof are designed, as appropriate, depending on the measuring method, the material characteristics of the aperture array structure, the frequency of the electromagnetic wave used, and so on. Thus, it is difficult to generalize respective ranges of those parameters, and the ranges of those parameters are not limited to the above-mentioned ranges.

The aperture array structure is preferably made of a metal. Examples of the metal include a metal capable of being coupled to a functional group, such as a hydroxy group, a thiol group, or a carboxyl group, of a compound containing that functional group, a metal allowing a functional group, such as a hydroxy group or an amino group, to be coated on the surface of the metal, and an alloy of those metals. Practical examples of the metals are gold, silver, copper, iron, nickel, chromium, silicon, germanium, etc. Of those examples, gold, silver, copper, nickel, and chromium are preferable. Nickel and gold are more preferable.

Attachment of Liquid to Aperture Array Structure

Measurement sensitivity is increased by directly or indirectly attaching a liquid to at least a part of the first principal surface that is one principal surface of the aperture array structure. When the specimen is a solid, a paste or the like, the liquid is usually separate from the specimen, but the liquid itself may be the specimen. Preferably, the aperture array structure is arranged such that the first principal surface lies substantially horizontally, and that the first principal surface provides the upper surface of the aperture array structure.

Hitherto, the measurement has been made based on a change in frequency characteristics obtained with the aperture array structure, the change being attributable to only the presence or the absence of the specimen. In contrast, since a liquid is attached to the aperture array structure in the present invention, characteristics of the specimen affect the surface tension of the liquid, etc. This changes a place where the liquid is present in the aperture array structure, and amplifies the influence on the frequency characteristics obtained with the aperture array structure. As a result, measurement sensitivity increases. It is to be noted that the liquid 3 is attached to the first principal surface side of the aperture array structure 1 in a state open to an atmosphere under air pressure.

Figure 2:
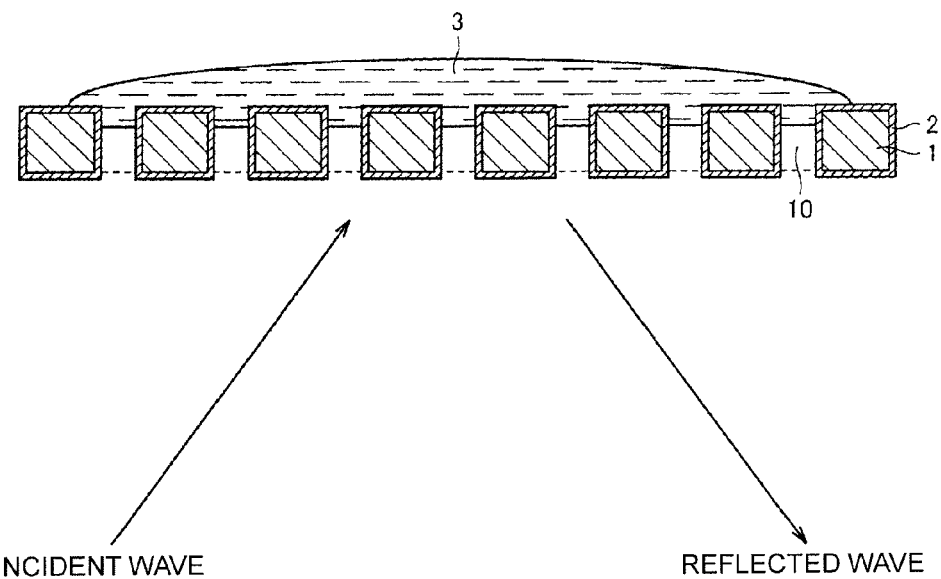
FIG. 2 is a schematic sectional view to explain one example of the measuring method according to the present invention.
Figure 3:
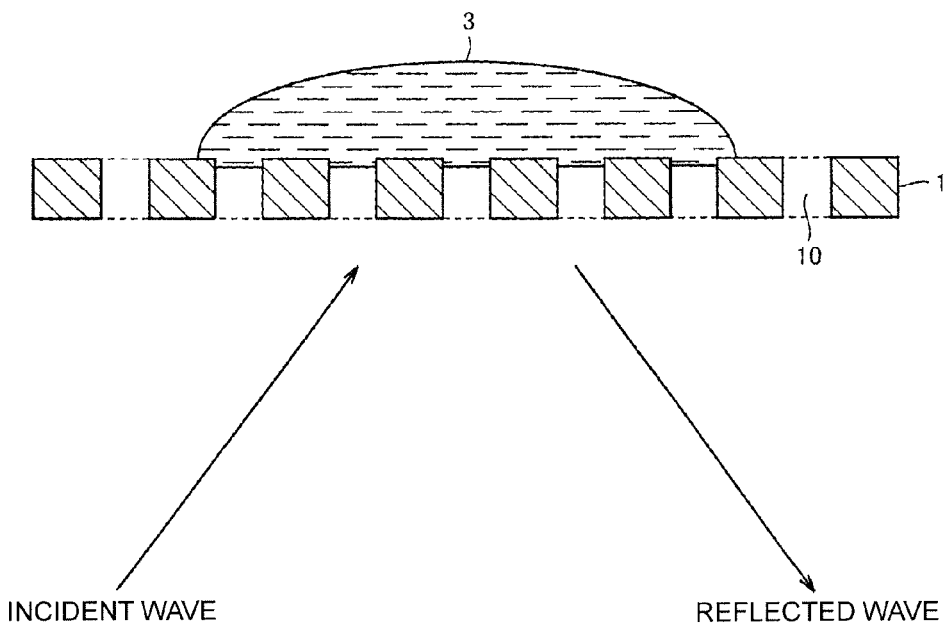
FIG. 3 is a schematic sectional view to explain the one example of the measuring method according to the present invention.

One example of the present invention will be described below with reference to FIGS. 2 and 3. FIG. 3 illustrates the case where the liquid 3, e.g., water, is dripped onto an upper surface (first principal surface) of a aperture array structure 1 that is highly hydrophobic. FIG. 2 illustrates the case where a highly-hydrophilic specimen 2 is attached to the surface of the aperture array structure 1 and a liquid 3, e.g., water, is dripped onto the upper surface (first principal surface) side.

Because the specimen 2 is present on the surface of the aperture array structure 1 (FIG. 2), the surface tension of the liquid 3 is reduced from that in the case where the specimen 2 is not present (FIG. 3), and the place where the liquid 3 is present on the aperture array structure 1 is changed. More specifically, as illustrated in FIGS. 2 and 3, the degree of sinking of the liquid 3 into the apertures 10 of the aperture array structure 1 is changed (the degree of sinking of the liquid 3 is larger in FIG. 2 than in FIG. 3), whereby the frequency characteristics obtained with the aperture array structure 1 are also changed. Thus, the presence or the absence of the specimen, etc. can be measured with higher sensitivity and higher efficiency based on an amount of the change in the frequency characteristics.

When the liquid is separate from the specimen, a real part of a complex refractive index of the liquid is preferably larger than that of the specimen. Furthermore, an imaginary part of the complex refractive index of the liquid is preferably larger than that of the specimen. More preferably, both the real part and the imaginary part of the complex refractive index of the liquid are larger those of the specimen.

In general, a change in the complex refractive index near the aperture array structure attributable to a change in location of the liquid is larger than a change in the complex refractive index near the aperture array structure attributable to the presence of the specimen itself because the complex refractive index of the liquid (particularly water) is larger than that of the specimen. Accordingly, the measurement sensitivity is increased. Even when the amount of the specimen is minute, there is a sufficient change in the complex refractive index near the aperture array structure attributable to a change in location of the liquid by attaching the liquid in a predetermined amount to the aperture array structure. Hence the measurement sensitivity is also increased in such a case.

In the present invention, the specimen can be held on the aperture array structure by optionally employing various known methods. For example, the specimen may be directly attached to the aperture array structure or may be attached to the aperture array structure with, e.g., a specific adsorptive film interposed therebetween.

When the liquid is separate from the specimen, direct attachment of the specimen to the aperture array structure can be practiced, for example, by a method of directly forming chemical coupling between the surface of the aperture array structure and the specimen, or a method of preparing an aperture array structure having a surface to which a host molecule is coupled in advance, and coupling the specimen coupled to the host molecule. Examples of the chemical coupling include covalent coupling (e.g., covalent coupling between a metal and a thiol group), Van der Waals coupling, ionic coupling, metal coupling, and hydrogen coupling. Of those examples, the valence coupling is preferable. The term "host molecule" implies a molecule to which the specimen can be specifically coupled. Combinations of the host molecule and the specimen are, for example, an antigen and an antibody, a sugar chain and a protein, a lipid and a protein, a low-molecule compound (ligand) and a protein, a protein and a protein, as well as a single strand DNA and a single strand DNA.

Moreover, a coating film made of the specimen may optionally be formed on the surface of the aperture array structure by employing various known methods.

Preferably, a peak waveform appears in frequency characteristics, such as a reflectance spectrum, which is obtained with the measuring method of the present invention. Here, the term "peak waveform" implies a local peak that usually appears in a frequency region (cutoff region) of the reflectance spectrum, for example, where the transmittance of the electromagnetic wave is low.

The peak waveform appearing in the frequency characteristics is preferably generated with TE11-mode resonance of the aperture array structure (when each aperture is regarded as a waveguide). As an alternative, the peak waveform is preferably generated with reduction of TE10-mode resonance of the aperture array structure (when each aperture is regarded as a waveguide). The reason resides in that the peak waveform appearing in the frequency characteristics is sharpened and the sensitivity in the measurement of the specimen is increased.

In order to generate the peak waveform, the aperture array structure is preferably inclined relative to the propagating direction and the polarizing direction of the electromagnetic wave. Moreover, the peak waveform due to the TE11-mode resonance can also be generated by making the shape of the aperture of the aperture array structure not mirror-symmetric with respect to an imaginary plane, which is perpendicular to the polarizing plane of the electromagnetic wave. In the latter case, the peak waveform due to the TE11-mode resonance can be generated even when the aperture array structure is arranged perpendicularly to the propagating direction of the electromagnetic wave.

The above-mentioned mirror-asymmetric shape of the aperture is, for example, a shape including a projection or a cutout in a region defining the aperture of the periodic structure. In such a case, it is preferable that the projection is present at a position in the region defining the aperture of the periodic structure where the intensity of an electric field is relatively strong, or the cutout is present at a position where the intensity of an electric field is relatively weak, when the TE11-mode-like resonance is generated. As an alternative, the aperture may be formed to have a trapezoidal, convex, concave, polygonal, or a star-like shape when viewed from a direction perpendicular to the principal surface of the periodic structure, and the aperture array structure may be arranged such that the shape of the aperture of the aperture array structure is not mirror symmetric with respect to the imaginary plane, which is perpendicular to the polarizing plane of the electromagnetic wave.

EXAMPLES

The present invention will be described in more detail below in connection with EXAMPLES, but the present invention is not limited to the following EXAMPLES.

Example 1

The aperture array structure used in EXAMPLE 1 is a structure having such a shape as illustrated in the schematic plan view of FIG. 4. More specifically, the structure used here is a Ni plate with a thickness of 6 μm in which square through-holes, each having four sides with a length (denoted by d in FIG. 4) of 18 μm, are arrayed in a square lattice pattern at a lattice interval (denoted by s in FIG. 4) of 26 μm.

Figure 5:
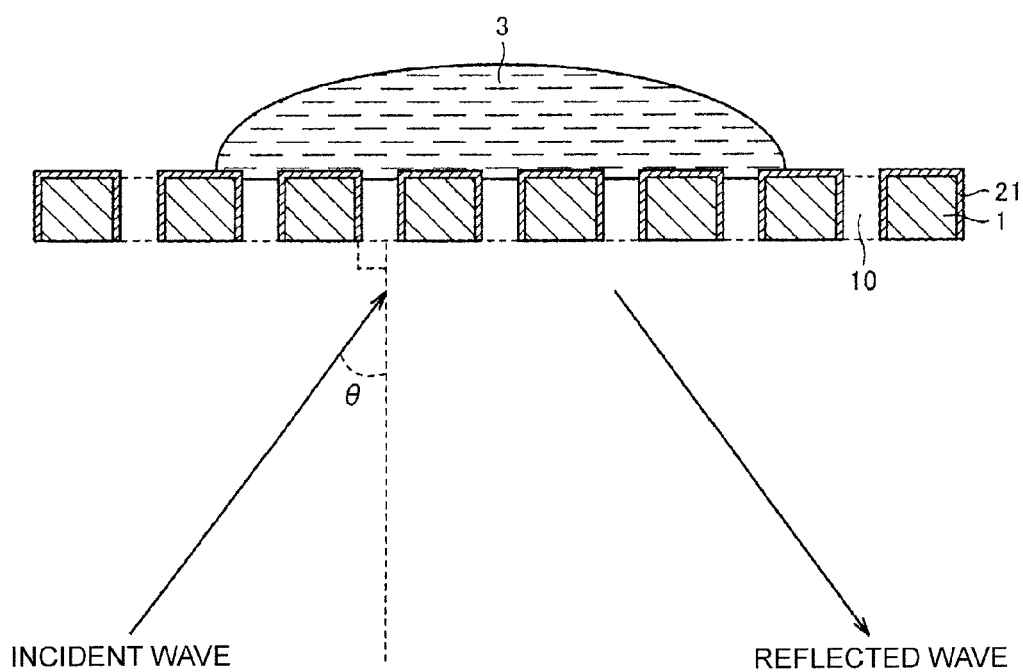
FIG. 5 is a schematic sectional view to explain a measuring method according to EXAMPLE 1.

FIG. 5 is a schematic sectional view illustrating a state where a specimen to be measured is attached to the surface of the above-described aperture array structure and a liquid is further dripped onto the specimen (i.e., a schematic sectional view taken along a plane perpendicular to the principal surface of the aperture array structure and parallel to the Y-direction in FIG. 4).

The specimen was a polyethylene (PE) film 21 and was attached to the surface of the aperture array structure 1 by a vapor deposition method. The complex refractive index of the polyethylene film 21 has a real part of about 1.585 and an imaginary part of about 0.01 in a measurement frequency region. With the result of TEM observation, the thickness of the polyethylene film 21 was 7 nm, and the polyethylene film 21 was attached mainly to one principal surface of the aperture array structure and lateral surfaces of apertures. Furthermore, 200 μL of pure water was dripped as the liquid 3 to an upper surface of the polyethylene film 21 attached to the aperture array structure 1. The liquid (pure water) 3 did not permeate to the lower side of the aperture array structure. In addition, the complex refractive index of the pure water has a real part of about 1.512 and an imaginary part of about 0.2830 in the measurement frequency region.

In the state described above, frequency characteristics of reflectance of an electromagnetic wave in the atmosphere were measured with the FT-IR. The electromagnetic wave was applied from such a direction that an angle θ (FIG. 5) formed by the propagating direction of the electromagnetic wave and the direction normal to the principal surface of the aperture array structure 1 was 20°. The measurement result is plotted in FIG. 7. It is to be noted that the reflectance in FIG. 7 of 100% represents a value measured when a mirror is placed instead of the aperture array structure.

Figure 6:
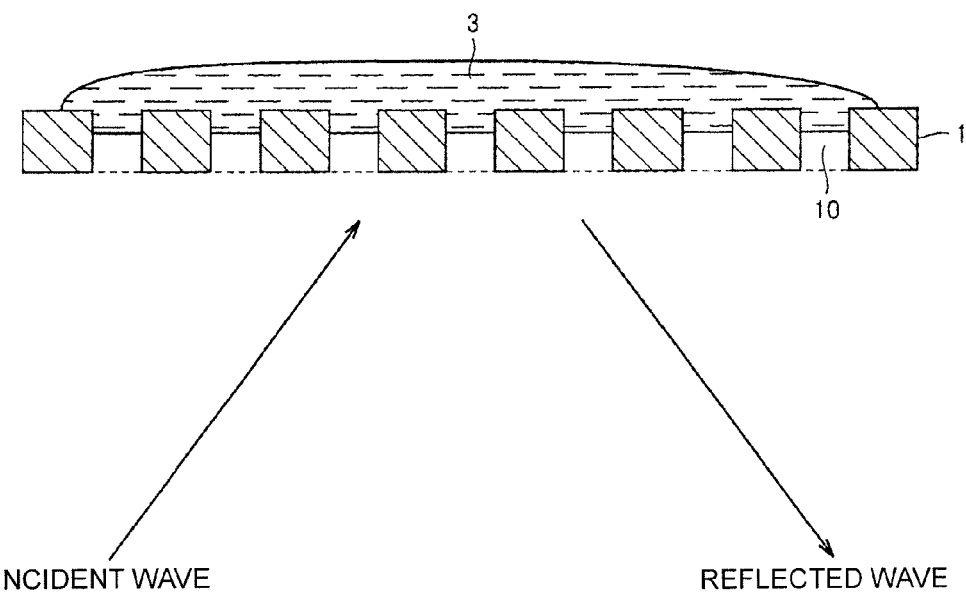
FIG. 6 is a schematic sectional view to explain the measuring method according to EXAMPLE 1.

As a control test, frequency characteristics of reflectance in a state of the polyethylene film being not attached, as illustrated in the schematic sectional view of FIG. 6, were also measured in a similar manner to that described above. More specifically, 200 μL of pure water was dripped as the liquid 3 to one surface (upper surface) of the aperture array structure 1. The pure water 3 did not leak to the other surface (lower surface) of the aperture array structure 1. In addition, the complex refractive index of the pure water 3 has a real part of about 1.512 and an imaginary part of about 0.2830 in the measurement frequency region. The measurement result is also plotted in FIG. 7.

Figure 7:
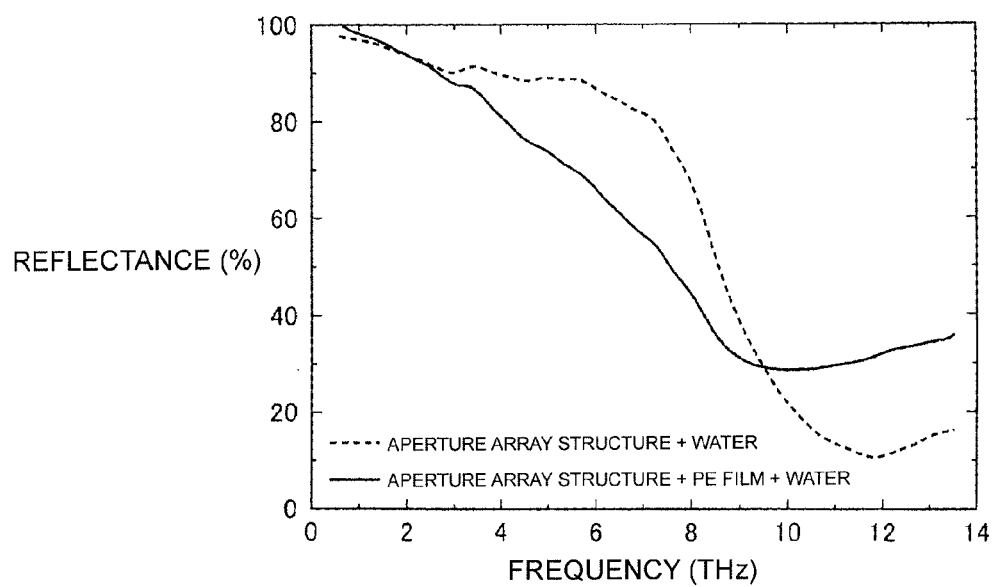
FIG. 7 is a graph depicting reflectance spectra obtained in EXAMPLE 1.

As seen from FIG. 7, the plots of the frequency characteristics obtained when the polyethylene film (specimen) is attached to the aperture array structure and when it is not attached thereto are different from each other. This implies that the presence or the absence of the specimen (polyethylene film) is detected. Moreover, an amount of the specimen can be calculated from comparison with a calibration curve prepared in advance based on frequency characteristics that have been obtained by measuring the specimen in various amounts.

Comparative Example

Figure 8:
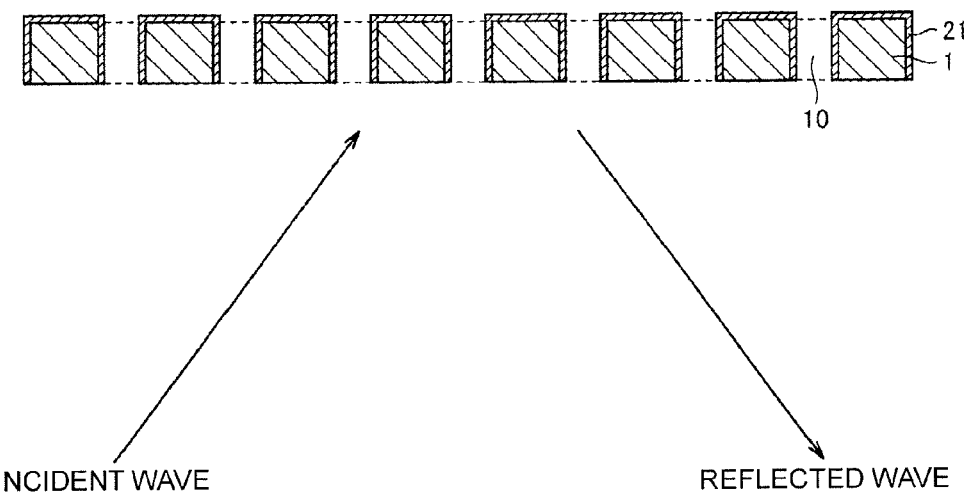
FIG. 8 is a schematic sectional view to explain a measuring method according to COMPARATIVE EXAMPLE.

In this COMPARATIVE EXAMPLE (representing the related art), measurement of a specimen was performed using an aperture array structure similar to that in EXAMPLE 1 without attaching a liquid. Stated in another way, frequency characteristics of reflectance in the atmosphere were measured with the FT-IR similarly to EXAMPLE 1 in a state where a polyethylene film (specimen) 21 was attached to the aperture array structure 1 without attaching a liquid thereto as illustrated in the schematic sectional view of FIG. 8.

The polyethylene (PE) film 21 as the specimen was attached to the surface of the aperture array structure 1 by a vapor deposition method. TEM observation showed that the thickness of the polyethylene film 21 was 7 nm, and the polyethylene film 21 was attached mainly to one principal surface of the aperture array structure 1 and lateral surfaces of apertures 10 (see FIG. 8). The measurement result is plotted in FIG. 10. It is to be noted that the reflectance in FIG. 10 of 100% represents a value measured when a mirror is placed instead of the aperture array structure.

Figure 9:
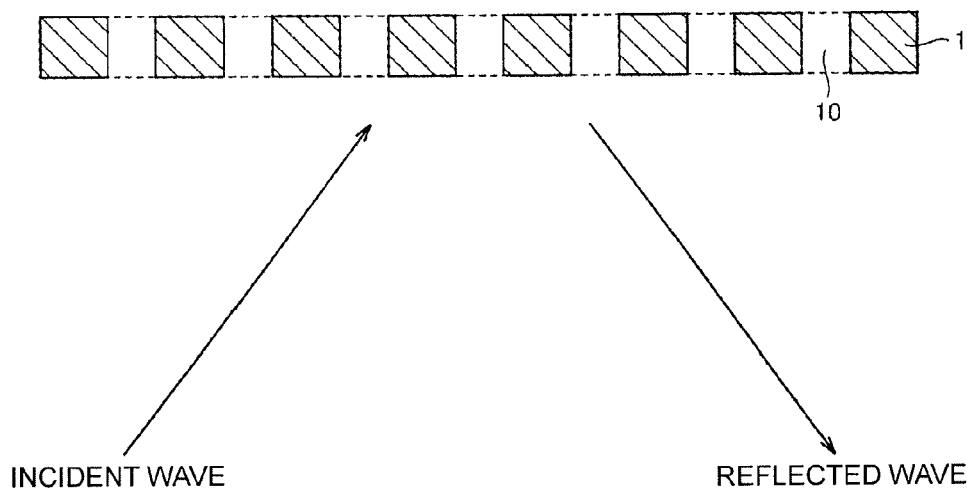
FIG. 9 is a schematic sectional view to explain the measuring method according to COMPARATIVE EXAMPLE.

As a control test, frequency characteristics of reflectance in a state of the polyethylene film being not attached, as illustrated in a schematic sectional view of FIG. 9, were also measured in a similar manner to that described above. The measurement result is also plotted in FIG. 10.

Figure 10:
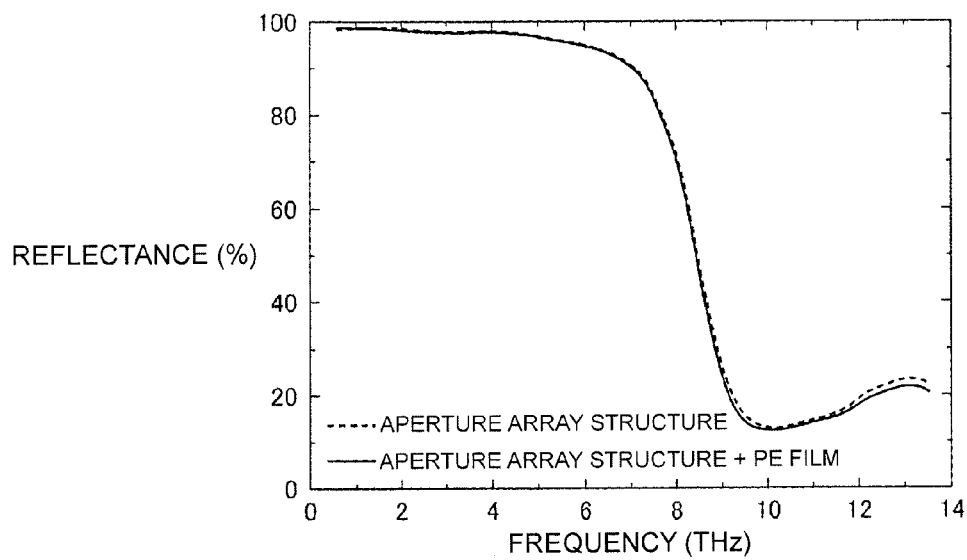
FIG. 10 is a graph depicting reflectance spectra obtained in COMPARATIVE EXAMPLE.

As seen from FIG. 10, the plots of the frequency characteristics obtained when the polyethylene film (specimen) is attached to the aperture array structure and when it is not attached thereto substantially matched with each other within the range of measurement error in the measuring apparatus. This implies that the presence or the absence of the polyethylene film (specimen) cannot be detected.

Example 2

Figure 11:
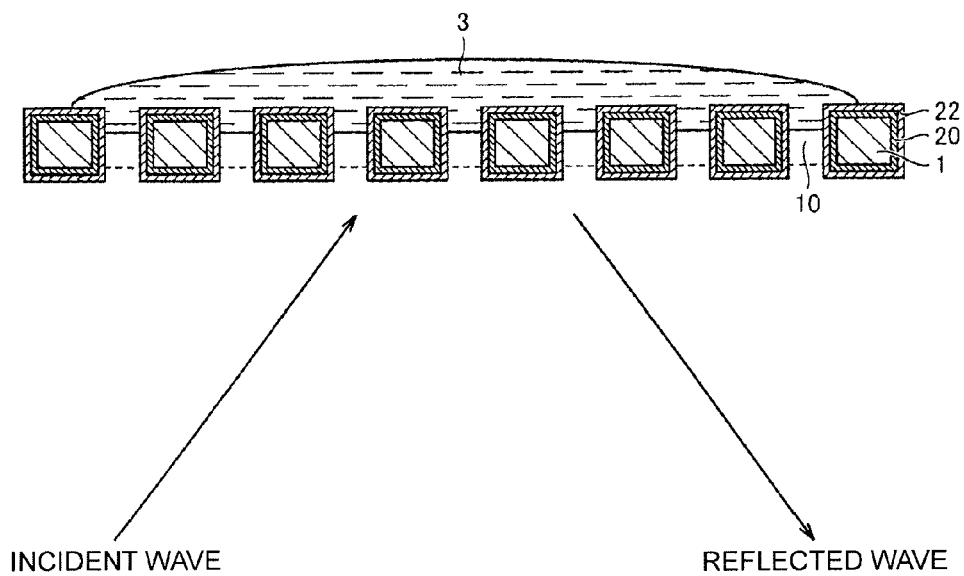
FIG. 11 is a schematic sectional view to explain a measuring method according to EXAMPLE 2.

In EXAMPLE 2, an aperture array structure similar to that in EXAMPLE 1 was employed. FIG. 11 is a schematic sectional view illustrating a state where a specimen 22 to be measured is attached to a specimen adsorptive film 20 fixed to the surface of the aperture array structure 1 and the liquid 3 is further dripped onto the specimen 2. The specimen adsorptive film 20 is a sugar chain high-molecule, and the specimen 22 is a protein. Furthermore, pure water was dripped as the liquid 3 onto the protein 22 that was attached to one surface (upper surface) of the aperture array structure 1. The liquid (pure water) 3 did not leak to the other surface (lower surface) of the aperture array structure 1. In addition, the complex refractive index of the pure water 3 has a real part of about 1.512 and an imaginary part of about 0.2830 in the measurement frequency region.

Figure 12:
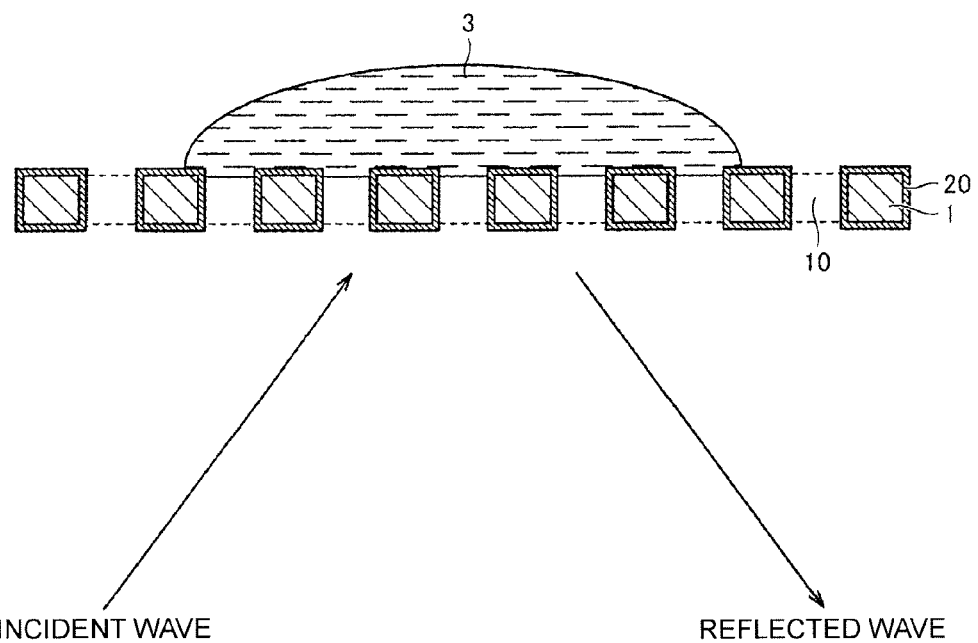
FIG. 12 is a schematic sectional view to explain the measuring method according to EXAMPLE 2.

The schematic sectional view of FIG. 12 illustrates the case of dripping the pure water 3 in a state where the specimen (protein) is not attached (i.e., a state where only the specimen adsorptive film 20 is fixed).

Comparing the state of FIG. 11 and the state of FIG. 12, the amount of pure water present near the surface of the aperture array structure and inside the apertures is larger in the state where the specimen is attached (FIG. 11) because hydrophillicity of the specimen (protein) is higher than that of the specimen adsorptive film (sugar chain high-molecule).

Example 3

The aperture array structure used in EXAMPLE 3 is a structure having such a shape as illustrated in the schematic plan view of FIG. 4. More specifically, the structure used here is a Ni plate with a thickness of 13 μm in which square through-holes, each having four sides with a length (denoted by d in FIG. 4) of 40 μm, are arrayed in a square lattice pattern at a lattice interval (denoted by s in FIG. 4) of 58 μm.

Figure 13:
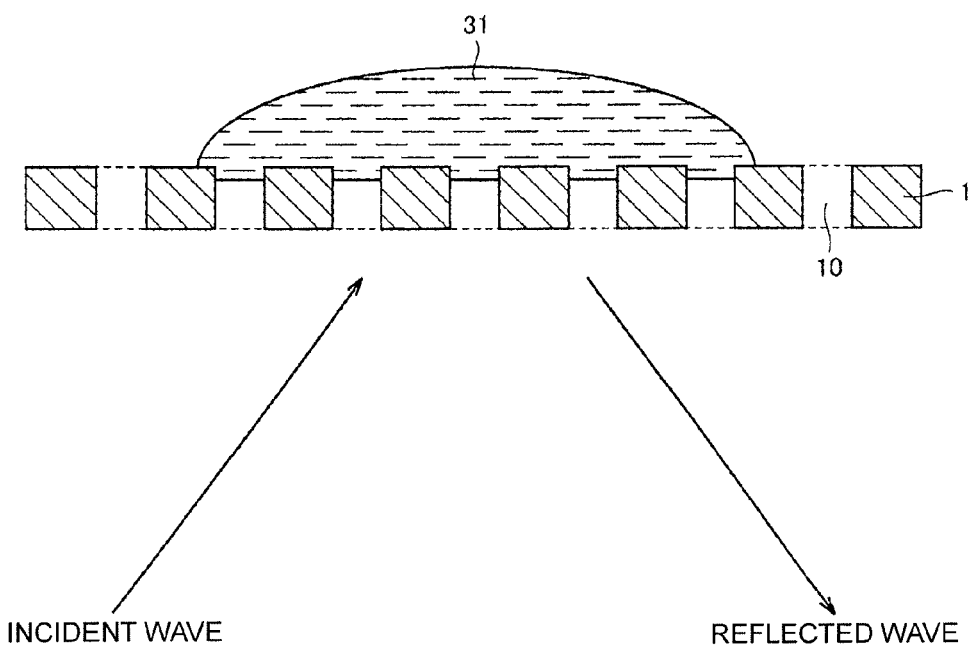
FIG. 13 is a schematic sectional view to explain a measuring method according to EXAMPLE 3.

FIG. 13 is a schematic sectional view illustrating a state where a liquid 31 as a specimen to be measured is attached to one principal surface (upper surface) of the aperture array structure 1. The liquid (specimen) 31 is 200 μL of aqueous solution of glycerin (glycerin concentration of 20, 40, 60, 80 or 100%) or pure water (glycerin concentration of 0%). The liquid (specimen) 31 did not leak to the other principal surface (lower surface) of the aperture array structure 1.

Figure 14:
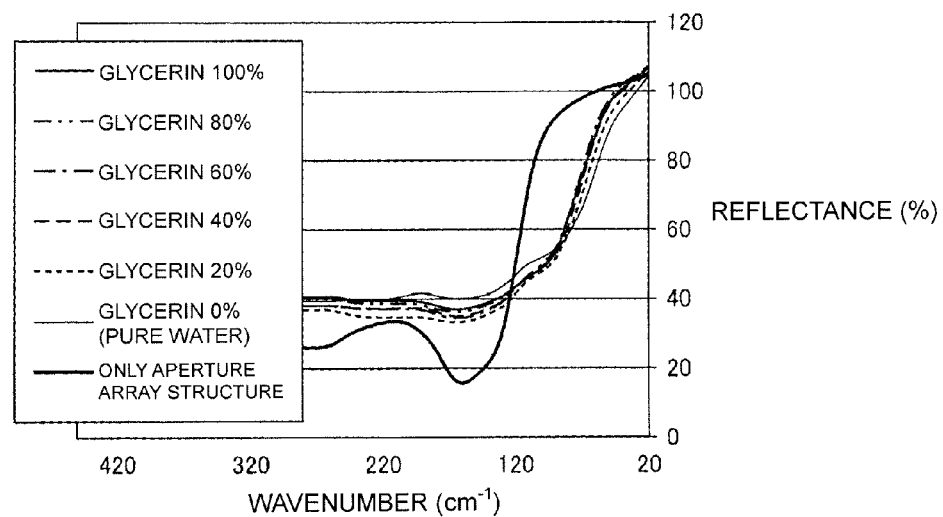
FIG. 14 is a graph depicting reflectance spectra obtained in EXAMPLE 3.

In the state described above, frequency characteristics of reflectance in the atmosphere were measured with the FT-IR similarly to EXAMPLE 1. FIG. 14 plots the measurement results of reflectance spectra. It is to be noted that the reflectance in FIG. 14 of 100% represents a value measured when a mirror is placed instead of the aperture array structure.

Figure 15:
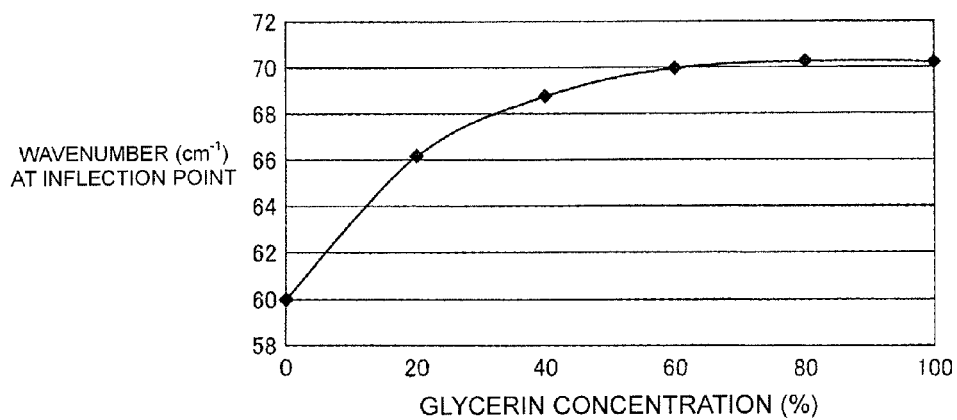
FIG. 15 is a graph depicting the relationship between glycerin concentration and wavenumber at a particular inflection point in the reflectance spectra in FIG. 14.

In FIG. 14, attention is paid to the relationship between an inflection point of each reflectance spectrum and glycerin concentration. FIG. 15 depicts the relationship between a wavenumber at the inflection point and the glycerin concentration. It is to be noted that the inflection point of the reflectance spectrum in FIG. 14 is defined at a wavenumber at which the quadratic differential of the reflectance spectrum in a wavenumber range of 120 cm$^{-1}$ or less is zero.

As seen from FIG. 15, the wavenumber at the inflection point increases as the glycerin concentration increases. This implies that a mixing ratio of the specimen (i.e., a mixed solution of pure water and glycerin) is detected. Moreover, the mixing ratio of the specimen can be calculated from comparison with a calibration curve prepared in advance based on frequency characteristics that have been obtained by measuring the specimen at various mixing ratios.

The embodiments and EXAMPLES disclosed here should be construed in all respects as illustrative and not restrictive. The scope of the present invention is defined not in the above description, but in the Claims. The present invention is purported to involve all modifications that fall within and that are equivalent to the Claims.

REFERENCE SIGNS LIST 1 aperture array structure, 10 aperture, 2 specimen, 20 specimen adsorptive film (sugar chain high-molecule), 21 polyethylene film (specimen), 22 protein (specimen), 3 liquid (pure water), 31 liquid (specimen), 7 laser, 70 half mirror, 71 mirror, 72, 73, 75 parabolic mirrors, 76 time delay stage, 77, 78 photoconductive elements, 80 power supply, 81 oscillator, 82 lock-in amplifier, 83 PC (personal computer), and 84 amplifier.

The invention claimed is:

1. A measuring method for measuring characteristics of a specimen comprising:
providing an aperture array structure having a specimen held thereto and having first and second principal surfaces, apertures, and a liquid directly or indirectly on at least a part of the first principal surface in a state open to an atmosphere under air pressure, wherein the apertures of the aperture array structure have a size which does not allow the liquid to leak from the first principal surface to the second principal surface, wherein the specimen is held on the aperture array structure, and wherein characteristics of the specimen change a place where the liquid is present on the aperture array structure,
applying an electromagnetic wave to the aperture array structure from the second principal surface, the second principal surface being positioned on the opposite side to the first principal surface to which the liquid is attached, and
detecting frequency characteristics of the electromagnetic wave reflected by the aperture array.

2. The measuring method according to claim 1, wherein when the aperture array structure is arranged with the first principal surface is substantially horizontal, the first principal surface is an upper surface of the aperture array structure, and the second principal surface is a lower surface of the aperture array structure.

3. The measuring method according to claim 2, wherein the specimen is attached to at least a part of the first principal surface of the aperture array structure, and the liquid is attached to a surface of the specimen.

4. The measuring method according to claim 3, wherein the liquid is water.

5. The measuring method according to claim 3, wherein the characteristic of the specimen detected is at least one member selected from the group consisting of presence or absence, amount, surface roughness, and film thickness of the specimen.

6. The measuring method according to claim 2, wherein the liquid attached to the first principal surface comprises the specimen.

7. The measuring method according to claim 6, wherein the liquid is aqueous.

8. The measuring method according to claim 6, wherein the characteristics of the specimen detected is at least one member selected from the group consisting of presence or absence of a solute, surface tension, concentration, and viscosity.

9. The measuring method according to claim 6, wherein the electromagnetic wave has a wavelength λ of 1 μm to 300 mm and a frequency of 1 GHz to 300 THz, and the angle formed by a propagating direction of the electromagnetic wave and a direction normal to the principal surface of the aperture array structure is 0° to 90°.

10. The measuring method according to claim 9, wherein the electromagnetic wave has a wavelength λ of 3 μm to 30 mm and a frequency of 10 GHz to 100 THz, and the angle is 0° to 45°.

11. The measuring method according to claim 10, wherein the electromagnetic wave has a wavelength λ of 30 μm to 3 mm and a frequency of 100 GHz to 10 THz.

12. The measuring method according to claim 1, wherein the specimen is attached to at least a part of the first principal surface of the aperture array structure, and the liquid is attached to a surface of the specimen.

13. The measuring method according to claim 12, wherein the liquid is water.

14. The measuring method according to claim 12, wherein the characteristic of the specimen detected is at least one member selected from the group consisting of presence or absence, amount, surface roughness, and film thickness of the specimen.

15. The measuring method according to claim 1, wherein the liquid attached to the first principal surface comprises the specimen.

16. The measuring method according to claim 15, wherein the liquid is an aqueous solution.

17. The measuring method according to claim 15, wherein the characteristics of the specimen detected is at least one member selected from the group consisting of presence or absence of a solute, surface tension, concentration, and viscosity.

18. The measuring method according to claim 1, wherein the characteristics of the specimen detected comprises changes in the frequency characteristics of reflectance of the electromagnetic wave reflected by the aperture array structure.

19. The measuring method according to claim 1, wherein the wavelength of the electromagnetic wave applied is not less than $1/10$ and not more than 10 times (a) a length of the apertures on the first principal surface in the polarization direction of the applied electromagnetic wave, and (b) the interval between said apertures.

20. The measuring method according to claim 1, wherein the aperture array structure is inclined relative to the propagating direction and the polarizing direction of the electromagnetic wave.

* * * * *